United States Patent [19]

van der Jagt

[11] Patent Number: Plant 6,067

[45] Date of Patent: Dec. 22, 1987

[54] CHRYSANTHEMUM NAMED "RESIDENT"

[75] Inventor: Martinus van der Jagt, Ter Aar, Netherlands

[73] Assignee: Chrysanthemum Breeders Association NV, Netherlands Antilles

[21] Appl. No.: 781,994

[22] Filed: Sep. 30, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Parkhurst & Oliff

[57] ABSTRACT

The present invention is a new and distinct variety of Chrysanthemum of a white anemone type with a yellow cushion.

3 Drawing Figures

BACKGROUND OF THE INVENTION

The present invention comprises a new and distinct cultivar of Chrysanthemum plant which is a cross of unknown parents. The invention was discovered by Martinus van der Jagt in May 1983 at Paradijsweg 88, Ter Aar, Holland. The invention has been asexually reproduced by cuttings at the same location. The new cultivar has been found to retain its distinctive characteristics through successive propagations.

BRIEF DESCRIPTION OF THE DRAWINGS

The present invention of a new and distinct variety of Chrysanthemum is shown in the accompanying drawings, the color being as nearly true a possible with color photographs of this type.

FIG. 1 shows the full bloom of the new cultivar.

FIG. 2 shows various stages of bloom of the new cultivar.

FIG. 3 shows the foliage and stem of the new cultivar.

DESCRIPTION OF THE INVENTION

This new variety of Chrysanthemum is of the botanical classification *Chrysanthemum morifolium* named "Resident". When grown in the vicinity of, Ter Aar, Holland, it has a response time of approximately 9 weeks. This new variety produces big white anemone type blooms having a 2 weeks performance. This new variety of Chrysanthemum has been found to retain its distinctive characteristics throughout successive propagations and may be planted under greenhouse conditions. in Holland between weeks 50 and 36.

The following is a description of the plant and characteristics that distinguish it over related known variety and its antecedents:

Bud:
- *Size.*—Large.
- *Form.*—Oval, flat.
- *Color.*—Cream white (like Chartreuse green) RHS 663/3.

Botanical classification: *Chrysanthemum morifolum.*

Bloom:
- *Size.*—Large.
- *Fully expanded.*—7-9 cm.
- *Borne.*—Single.
- *Stems.*—Strong.
- *Form.*—Anemone type.

- *Permanence.*—18 days.

Color:
- *Center of flower.*—(Cushion) dresden yellow, RHS 64/1.
- *Base of petals.*—Pure white.
- *Inside of petals.*—Pure white.
- *Reverse of petals.*—Pure white.
- *Outer petals.*—Pure white.
- *Tonality from a distance.*—White anemone type with yellow cushion. Nice formed petals.
- *Discoloration.*—None. Just white.

Petals:
- *Texture.*—Two rows.
- *Number.*—25-30.
- *Arrangement.*—Somewhat imbricated.
- *Persistence.*—Good.
- *Fragrance.*—Typical Chrysanthemum.

Reproductive organs:
- *Stamen.*—Not so much, long.
- *Pollen.*—None to few.
- *Styles.*—Columnar.
- *Length.*—Long.
- *Stigmas.*—Normal.
- *Ovaries.*—Enclosed in calyx.

Plant:
- *Form.*—Herbaceous.
- *Growth.*—Normal.
- *Height.*—Medium.
- *Penduncle.*—Strong.

Foliage:
- *Color.*—Normal.
- *Size.*—Large.
- *Quantity.*—Normal to less.
- *Shape.*—Pointed-oval.
- *Texture.*—Hard.
- *Ribs and veins.*—Ordinary.
- *Edge.*—Undulated.
- *Leaf underside.*—Smooth.

In the description above color references are made to The Horticultural Colour Chart I & II issued by The British Colour Council in collaboration with The Royal Horticultural Society, Copyright Robert F. Wilson, Vol I, 1938; Vol II, 1941, printed by Henry Stone & Son LTD. Banbury, England.

I claim:

1. A new and distinctive variety of Chrysanthemum as described and illustrated in the foregoing specification and accompanying drawings.

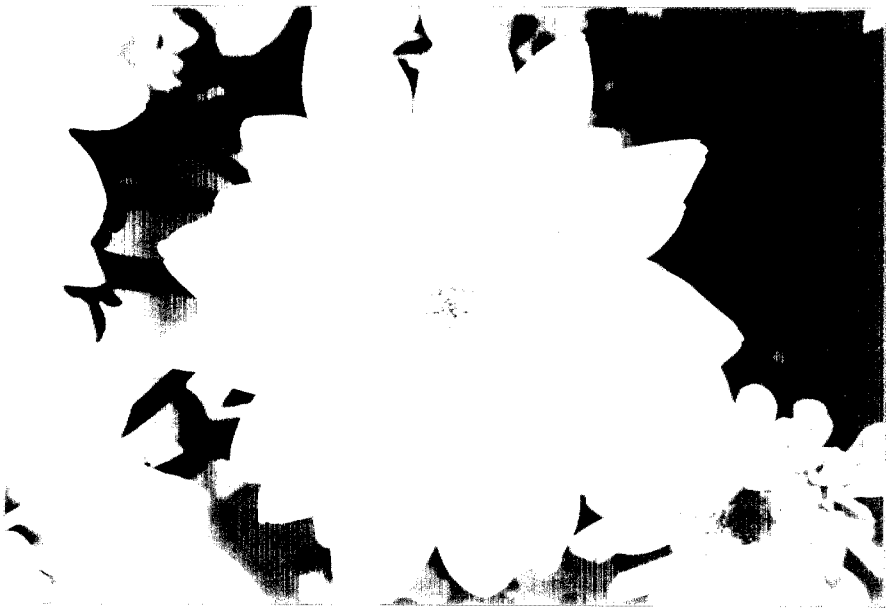

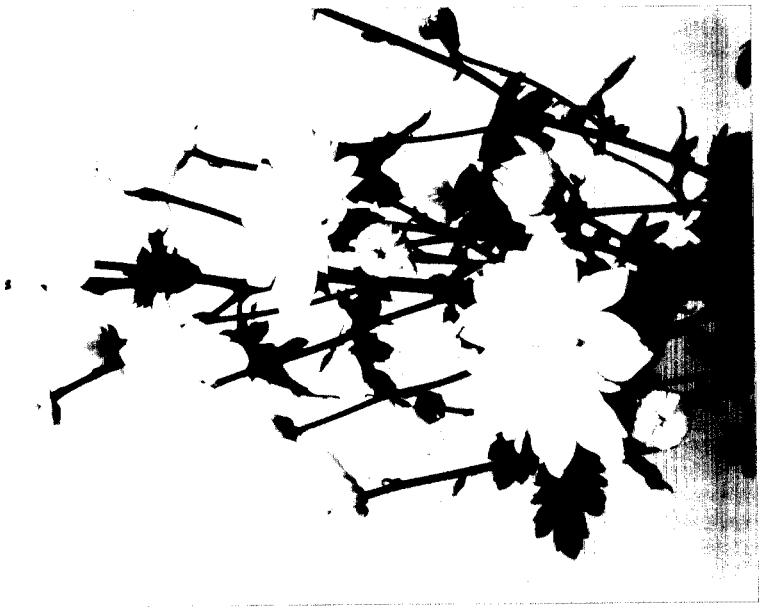
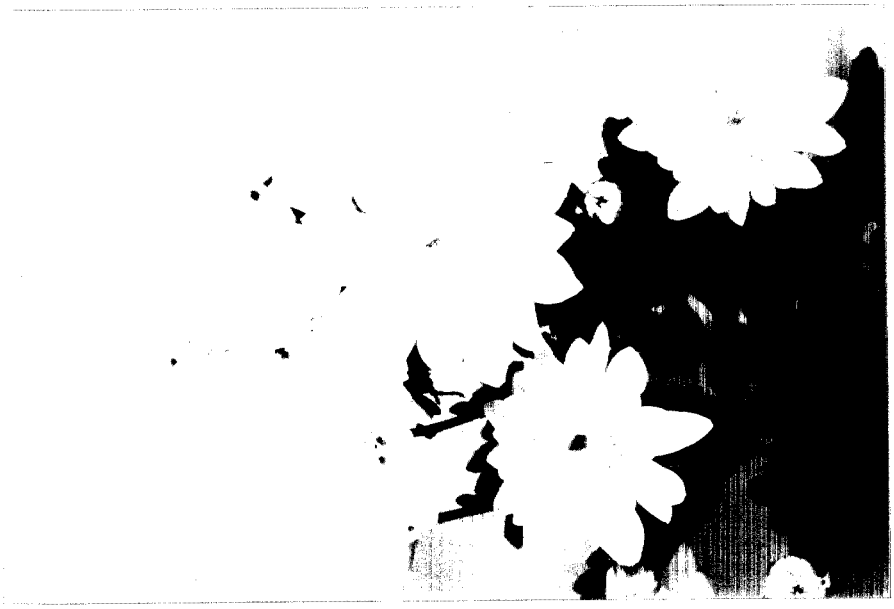

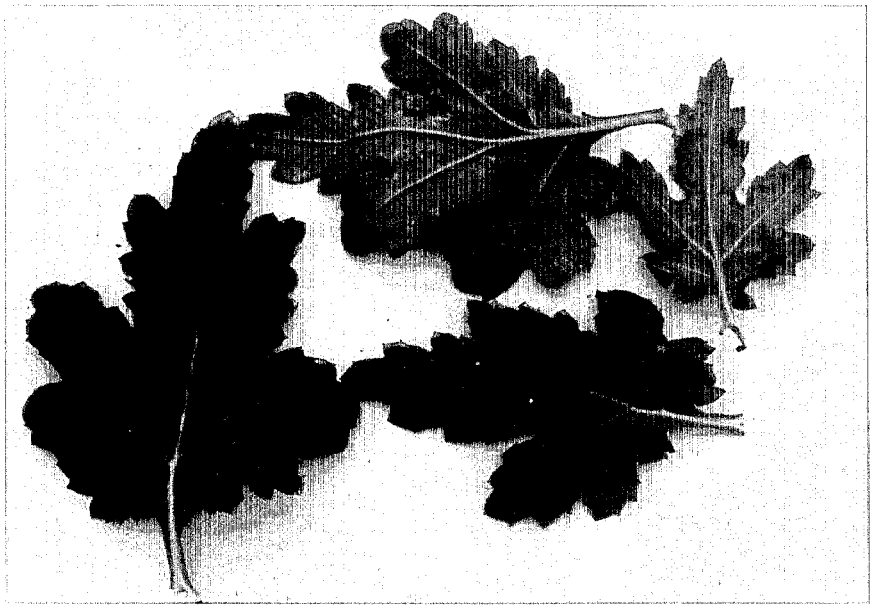

* * * * *